(12) United States Patent
Her et al.

(10) Patent No.: US 7,365,192 B2
(45) Date of Patent: Apr. 29, 2008

(54) PREPARATION METHOD OF VALIENAMINE FROM ACARBOSE AND/OR ACARBOSE DERIVATIVES USING TRIFLUOROACETIC ACID

(75) Inventors: Youl Her, Gyeonggi-Do (KR); Jin-Hwan Oh, Daejeon (KR)

(73) Assignee: B T Gin, Inc., Majeon-Ri, Chubu-Myeon, Geumsan-Gun, Chungcheongnam-Do (KR)

( * ) Notice: Subject to any disclaimer, the term of this patent is extended or adjusted under 35 U.S.C. 154(b) by 326 days.

(21) Appl. No.: 10/519,519

(22) PCT Filed: Nov. 23, 2002

(86) PCT No.: PCT/KR02/02198

§ 371 (c)(1), (2), (4) Date: Aug. 1, 2005

(87) PCT Pub. No.: WO04/000782

PCT Pub. Date: Dec. 31, 2003

(65) Prior Publication Data

US 2005/0272674 A1    Dec. 8, 2005

(30) Foreign Application Priority Data

Jun. 25, 2002    (KR) .................... 10-2002-0035683
Aug. 29, 2002    (KR) .................... 10-2002-0051511

(51) Int. Cl.
*C07H 1/00*     (2006.01)
*C07H 3/00*     (2006.01)
*C08B 37/00*    (2006.01)
*C07C 211/00*   (2006.01)

(52) U.S. Cl. .................... 536/124; 536/123.1; 514/54; 514/61; 564/462

(58) Field of Classification Search ................ 536/124, 536/123.1; 514/54, 61; 564/462
See application file for complete search history.

(56) References Cited

FOREIGN PATENT DOCUMENTS

WO    WO 2004000782 A1    12/2003

OTHER PUBLICATIONS

Tatsuta, Kuniaki, Mukai, Hiroshi and Takahashi, Masaaki, "Novel Synthesis of Natural Pseudo-aminosugars, (+)-Valienamine and (+)-Validamine", The Journal of Antibiotics, vol. 53 No. 4, pp. 430-435, Apr. 2000.

Yoshikawa, Masayuki, Cha, Bae Cheon, Okaichi, Yoshihiko, Takinami, Yoshihiko, Yokokawa, Yoshihiro and Kitagawa, Isao, "Syntheses of Validamine, EPI-Validamine, and Valienamine, Three Optically Active Pseudo-Amino-Sugars, From D-Glucose", Communications to the Editor, Chem. Pharm. Bull, vol. 36, pp. 4236-4239, 1988.

*Primary Examiner*—Shaojia Anna Jiang
*Assistant Examiner*—Michael C. Henry
(74) *Attorney, Agent, or Firm*—Barlow, Josephs & Holmes, Ltd.

(57) ABSTRACT

The present invention provides a preparation method of valienamine from acarbose or acarbose derivatives using organic acid TFA (trifluoroacetic acid). By using the method of the present invention, valienamine, the core precursor of voglibose which is a strong retardant of α-glucosidase and which is used for the cure of diabetes, can be produced in large quantities by using selective hydrolysis from acarbose or acarbose derivatives using TFA.

6 Claims, 4 Drawing Sheets

PREPARATION METHOD OF VALIENAMINE FROM ACARBOSE AND/OR ACARBOSE DERIVATIVES USING TRIFLUOROACETIC ACID

CROSS-REFERENCE TO RELATED APPLICATIONS

This application claims the benefit of PCT International Application Number PCT/KR2002/002198 under 35 U.S.C. §371.

BACKGROUND OF THE INVENTION

1. Field of the Invention

The present invention relates to a method of producing valienamine and, more particularly, to a method of producing valienamine at a substantially high conversion rate. The method involves mass producing valienamine by way of selective hydrolysis by using TFA from acarbose or acarbose derivatives, and then removing its by-products therefrom, i.e., monosaccharides, disaccharides, and trisaccharides.

2. Brief Description of the Related Art

The conventional art relating to commercial production of valienamine can be divided into two types. The first type relates to a method of direction production of valienamine by using microorganism fermentation, and the second type relates to a method of production of validamycin, a derivative of valienamine, by degradation by using other microorganisms.

Validamycin derivatives basically include a valienamine moiety which selectively binds with validamine or valiolamine. Moreover, a validamycin derivative is a pseudotrisaccharide compound which is glucose bonded in chain.

The validamycin compound is an antibiotic used for germicide for rice-cultivated land in East Asia which is produced among other methods by culturing *Streptomyces hygroscopicus*, a soil microorganism. Here, the validamycin compound contains a small amount of intermediate valienamine which is then separated out via a column.

As for another method for producing valienamine, there is a method of separating validamycin by using a microorganism, *F. saccharophilum*, etc. The method involves using validamycin as a substrate or medium and adding it to the liquid mixed with microorganisms; culturing them for a certain period of time; and then inducing separation of validamycin by microorganisms; and then obtaining validamycin by separation via a column. Yet, the two methods have disadvantages in that they take too much time for microorganism fermentation with not much higher yield.

Another compound which has a valienamine moiety is acarbose. Acarbose is obtained from secondary metabolic products of *Actinoplanes* sp., which is one type of soil microorganisms. It is currently being used as a treatment for diabetes, since it has inhibition effects on α-amylase. However, as of yet, there is no disclosure of the process of commercial or mass production of valienamine by using acarbose as a raw material.

As for methods of producing valienamine, reported in academia, there is a chemical method of producing valienamine by using N-bromosuccinimide (NBS) with validamycin as raw material. However, as this method uses dimethyl sulfoxide (DMSO) as solvent, it suffers from difficulties during purification and separation processes of byproducts, in addition to its low yield. Moreover, there is an ongoing research into the production method of valienamine using organic and inorganic acid, such as sulfuric acid, hydrochloric acid, and acetic acid. Yet, the method is not practical since it is limited to the extent of hydrolysis of only one terminal saccharide. Moreover, there was an attempt to produce valienamine by way of organic synthesis, but it currently is in a standstill due to the inefficiency of purification and organic synthesis processes.

There is a production method of valienamine by pre-synthesis by enzyme, which is being actively pursued in recent years. This is a method of producing valienamine by using an inexpensive substrate by finding valienamine synthesis and related enzymes expressed by a strain. However, there are many difficulties, such as determination of the degree of activity and the expression according to a gene probe. So, the current production is rather difficult.

As stated above, the production of valienamine in vitro by purification enzymes or chemicals has not yet been commercialized, and so up to now, valienamine has been mainly synthesized and produced by hydrolyzing validoxylamine and validamycin by using the strains, *Pseudomonas denitrificans* and *Flavobacterium saccharophilum*. Japanese Patent No. 57,054,593 discloses a reaction of converting validoxylamine and validamycin by using microorganisms. This is a method of synthesizing and producing valienamine by using *Flavobacterium saccharophilum* by reacting 1-5 wt. % mixture of validoxylamine and validamycin for about 24 to about 200 hours at reaction conditions of 20-45° C. and pH 5-8.

SUMMARY OF THE INVENTION

The present invention purports to provide a method of producing valienamine at a substantially high conversion rate. The method involves first mass producing valienamine through selective hydrolysis from acarbose or acarbose derivatives by using TFA, and then removing the byproducts, i.e., monosaccharides, disaccharides, and trisaccharides.

To achieve said objectives, the present invention involves a method of producing valienamine from acarbose or acarbose derivatives by using trifluoroacetic acid (TFA). In particular, the present invention provides a method of producing valienamine by using a reaction substrate of final concentration of 0.2-10% acarbose or acarbose derivatives, and a reaction solvent of 10-60% TFA solution.

If the final concentration of acarbose or its derivatives is less than 0.2%, or that of TFA exceeds 60%, the production cost per unit increases. On the other hand, if the final concentration of acarbose or its derivatives exceeds 10%, or that of TFA is less than 10%, the yield therein decreases.

Moreover, the present invention provides a method of producing valienamine from acarbose or acarbose derivatives by using TFA, which is characterized by reacting it for about 1 to about 24 hours at about 80 to about 120° C., or by using a high-temperature and high-pressure autoclave, which can reduce reaction time to one hour and increase its yield up to 96%.

Accordingly, the present invention can yield valienamine with an amine group of $NH_2$ or $NH^+_3$ at its carbon chain.

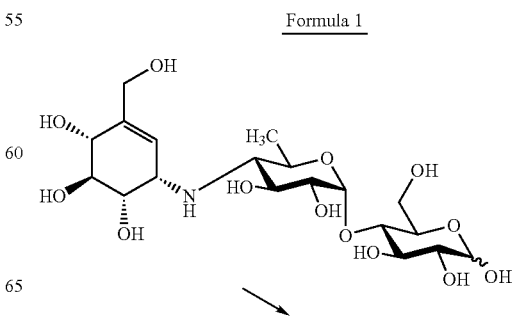

Formula 1

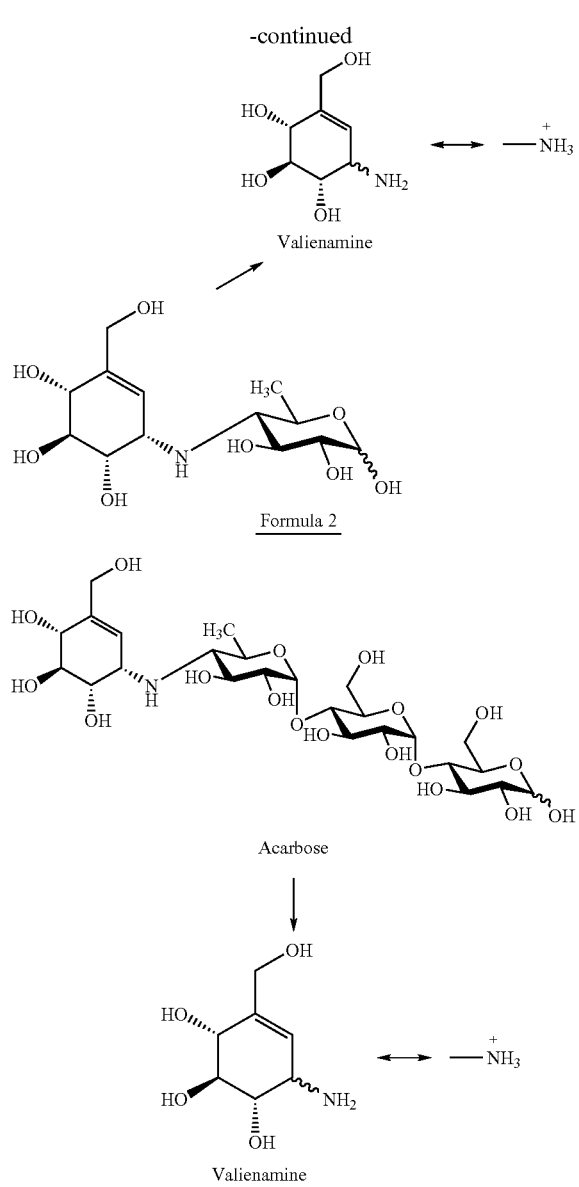

Formula 2

Acarbose

Valienamine

Moreover, according to the present invention, an acarbose derivative is a compound having one, two, four, five or more saccharides bonded to a carbon chain, but generally refers to a derivative of one or two saccharides.

Valienamine is known to have maltase and sucrase inhibition effects and to have antibiotic activity as against *Bacillus* species. Moreover, its intramolecular atom alignment is similar to that of alpha-D-glucose. The inhibition activity of alpha-glucosidase of valienamine is believed to be caused by structural similarity of valienamine to D-glucosyl cation. The D-glucosyl cation with an enzyme as a catalyst forms a half-chair conformation in a transition state, which is produced during hydrolysis of pyranoside.

As for compounds with a valienamine moiety, there are acarbose, and its derivatives, validoxylamine, validamycin, etc. Among these, acarbose is being widely used as an inhibitor for Type II diabetics. Acarbose and acarbose derivatives have different structures from the other two compounds (validoxylamine and validamycin), and their production methods are substantially different as well.

Compounds with a valienamine moiety, i.e., acarbose, and its derivatives, validoxylamine, and validamycin, are all potentially raw materials for valienamine. All of them are produced by fermentation by different bacteria strains, respectively. Among these, acarbose is being distributed as a diabetic treatment all over the world by a German pharmaceutical company, Bayer, Inc., along with Chinese and Japanese pharmaceutical companies. Acarbose is more expensive than validamycin but is easier to obtain in a pure raw material form. Accordingly, acarbose has the advantage of easy separation process, which makes it an appropriate raw material for valienamine. When using acarbose as a raw material, there is a problem of difficult purification by way of pigments from cleaved saccharide, but this can be easily resolved by using acarbose derivatives.

BRIEF DESCRIPTION OF THE DRAWINGS

The novel features that are characteristic of the present invention are set forth in the appended claims. However, the preferred embodiments of the invention, together with further objects and attendant advantages, will be best understood by reference to the following detailed description taken in connection with the accompanying drawings in which:

DETAILED DESCRIPTION OF THE PREFERRED EMBODIMENTS

Figure 1:
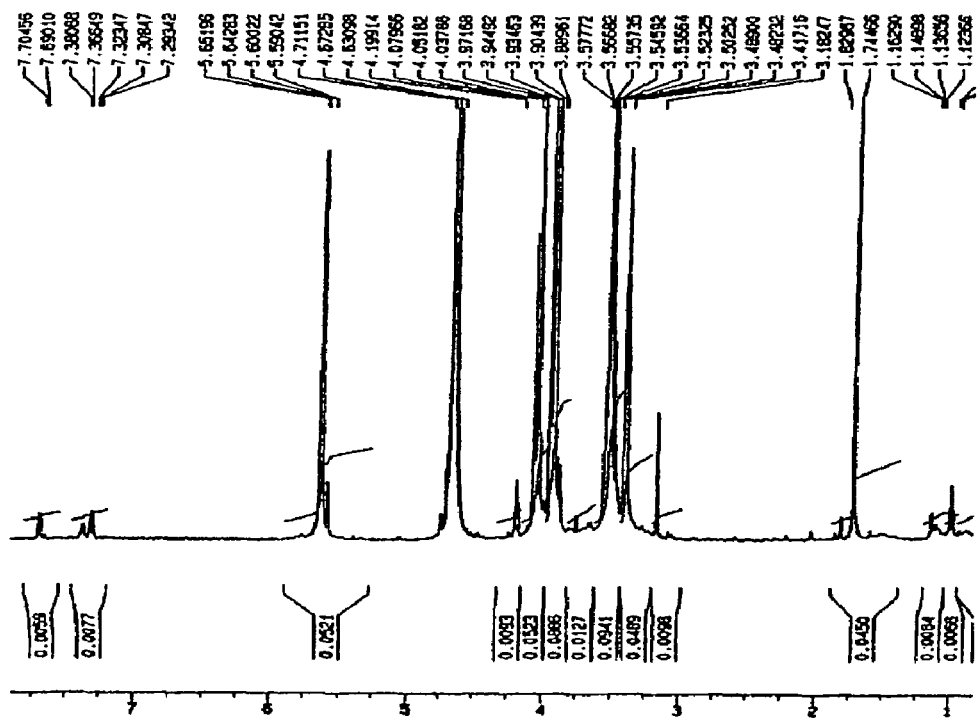
FIG. 1 is a hydrogen NMR spectrum of valienamine produced from acarbose by using TFA.
Figure 2:
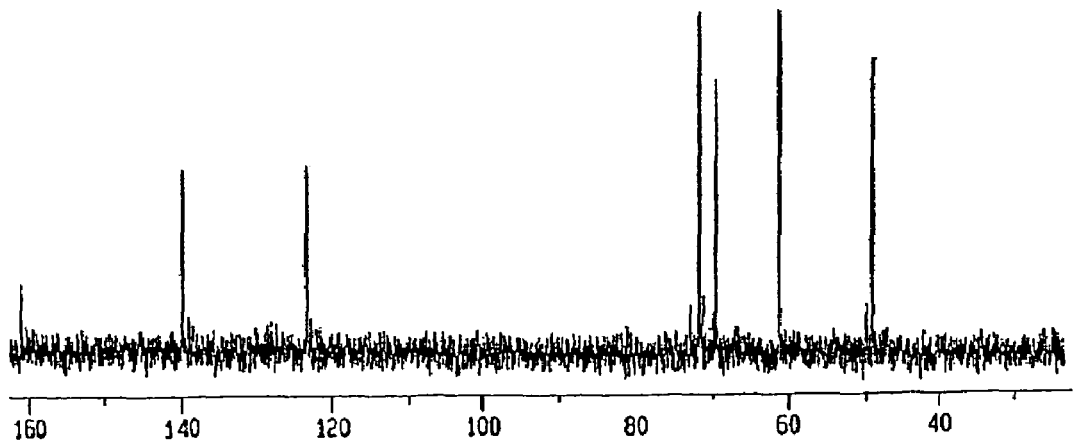
FIG. 2 is a carbon NMR spectrum of valienamine produced from acarbose by using TFA.
Figure 3:
FIG. 3 is a hydrogen NMR spectrum of valienamine produced from an acarbose derivative by using TFA.
Figure 4:
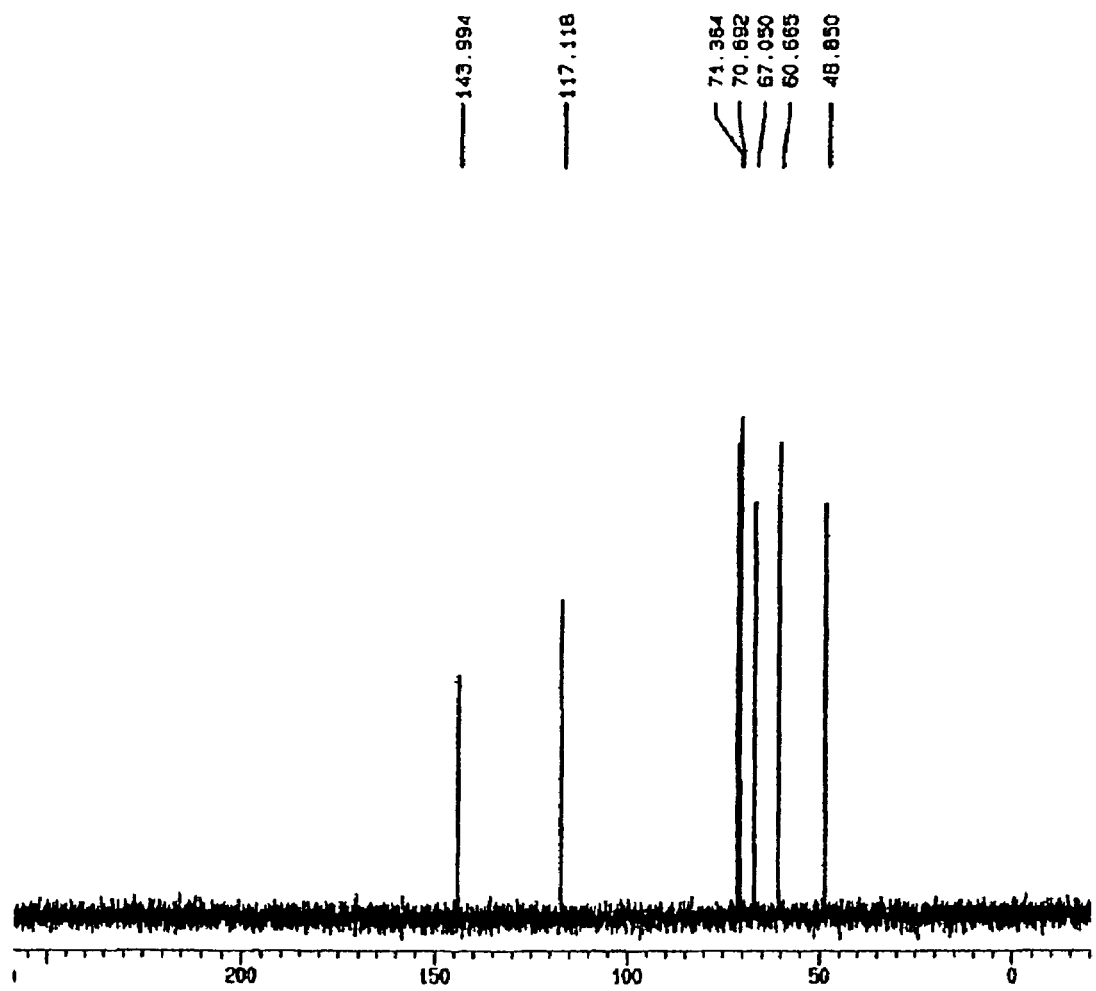
FIG. 4 is a carbon NMR spectrum of valienamine produced from an acarbose derivative by using TFA.
Figure 5:
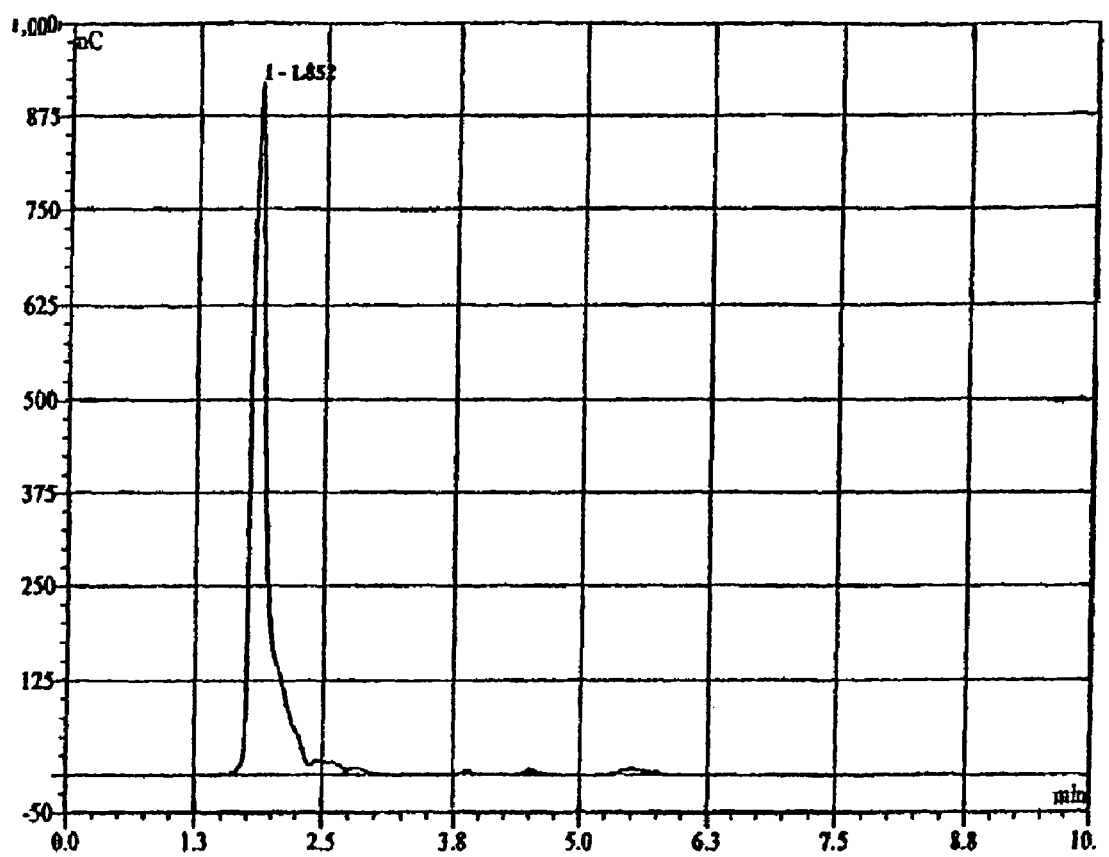
FIG. 5 is a graph of Bio-LC(HPLC) data of valienamine produced from an acarbose derivative by using TFA.

The present invention is further illustrated by the following examples, but these examples should not be construed as limiting the scope of the invention

EXAMPLE 1

Method Of Producing Valienamine Using TFA 10 g of pure acarbose were place into 10% TFA solution at 5% final concentration. At a reaction temperature of 100° C., it was reacted for 12 hours or more, followed by removal of TFA and water. Then, by using ion-exchange resins for purification, 2.02 g of valienamine were obtained respectively.

EXAMPLE 2

Method Of Producing Valienamine Using TFA 1 g of a pure acarbose derivative (monosaccharide and trisaccharide) were place into 10% TFA solution at 5% final concentration. At reaction temperature of 100° C., it was reacted for 12 hours or more, followed by removal of TFA and water. Then, by using ion-exchange resins for purification, 0.45 g and 0.31 g of valienamine were obtained, respectively.

EXAMPLE 3

Method Of Producing Valienamine

Using TFA By Using An Autoclave 10 g of pure acarbose were place into 10% TFA solution at 5% final concentration. While putting pressure using an autoclave, at a reaction temperature of 121° C., it was reacted for 30 minutes to 1 hour, followed by removal of TFA and water. Then, by using ion-exchange resins for purification, 2.1 g of valienamine were obtained.

EXAMPLE 4

Method Of Producing Valienamine

Using TFA By Using An Autoclave 1 g of a pure acarbose derivative (monosaccharide and trisaccharide) were place into 10% TFA solution at 5% final concentration. While putting pressure using an autoclave, at reaction temperature of 121° C., it was reacted for 30 minutes to 1 hour, followed by removal of TFA and water. Then, by using ion-exchange resins for purification, 0.46 g and 0.30 g of valienamine were obtained, respectively.

The hydrogen and carbon NMR spectrums with respect to the resultant products obtained as a result of the reactions of Examples 1 and 2 are as follows: $^1$H-NMR(D$_2$O) δ: 3.42 (1H, br s, H-1), 3.54(2H, Abq, J=13.6 Hz, H-7), 3.94(1H, d, J=6.79 Hz), 3.97(1H), 4.05(1H), 5.64(1H, d, J=4.6) $^{13}$C-NMR(D$_2$O) δ: 48.9(C-1), 61.2(C-7), 69.7(C-2), 71.7(C-4), 71.7(C-3), 123.4(C-6), 139.9(C-5).

By using the method of the present invention, valienamine can be produced from acarbose with a yield rate of about 50 to about 95%, or acarbose derivatives with a yield rate of about 70 to about 95%. Since hydrolysis is occurred on the α-binding adjacent to the amine moiety of valienamine, only monosaccharides, disaccharides, or trisaccharides are produced as byproducts. Due to this advantage, the refining process becomes simple making it possible to produce valienamine with high purity while reducing the pigments.

In addition, by using the method of the present invention, the voglibose, which is widely sold as a remedial agent of diabetes over the world including Korea, Japan and China, can be more easily produced cutting down the production cost. Also the invention can contribute to the development of valienamine derivatives which have better pharmaceutical activity, or which can be used on other types of disease.

It is appreciated by those skilled in the art that various changes and modifications can be made to the illustrated embodiments without departing from the spirit of the present invention. All such modifications and changes are intended to be covered by the appended claims.

What is claimed is:

1. A method of producing valienamine, comprising the steps of:
   providing at least one compound selected from the group consisting of acarbose, acarbose derivatives and combination thereof;
   introducing said compound into a solution of trifluoroacetic acid;
   reacting said compound and said trifluoroacetic acid to produce valienamine and byproducts.

2. The method of producing valienamine according to claim 1, wherein the method comprises reacting at a temperature of 80 degrees to 120 degrees Celsius for at least one hour to twenty-four hours.

3. The method of producing valienamine according to claim 1, wherein the method comprises reacting using an autoclave, pressure, and temperature greater than 120 degrees Celsius from 30 minutes to one hour.

4. The method of producing valienamine according to claim 1, wherein the method comprises using a range of 10% to 60% trifluoroacetic acid.

5. The method of producing valienamine according to claim 1, wherein the method comprises using a reaction substrate of final concentration of about 0.20% to 10% of acarbose or an acarbose derivative or combination thereof.

6. The method of producing valienamine according to claim 1, further comprising:
   removing byproducts to isolate valienamine; and
   purifying valienamine in presence of ion-exchange resins.

* * * * *